United States Patent [19]
Fleming et al.

[11] 4,081,597
[45] Mar. 28, 1978

[54] PROCESS FOR THE MANUFACTURE OF PYRAZOLONES FROM PYRAZOLIDONES

[75] Inventors: Ian George Cameron Fleming; Raymond Vincent Heavon Jones, both of Manchester, England

[73] Assignee: Imperial Chemical Industries Limited, United Kingdom

[21] Appl. No.: 750,158

[22] Filed: Dec. 13, 1976

[30] Foreign Application Priority Data

Dec. 24, 1975 United Kingdom ............... 52886/75

[51] Int. Cl.² ................. C07D 231/22; C07D 231/24; C07D 231/26
[52] U.S. Cl. ............... 548/363; 260/295 L; 260/305; 548/367
[58] Field of Search .............. 260/310 A, 295 L, 305; 548/363, 367

[56] References Cited
U.S. PATENT DOCUMENTS 1,723,545  8/1929  Finkelstein et al. ............. 260/310 A Primary Examiner—Natalie Trousof
Assistant Examiner—Jane T. Fan
Attorney, Agent, or Firm—Cushman, Darby & Cushman

[57] ABSTRACT

A process for manufacture of pyrazolones of the formula:

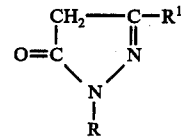

wherein R is an aromatic radical and $R^1$ is an alkyl, carboxylic acid, carbamoyl or carboxylic ester group which comprises treating a pyrazolidone of the formula:

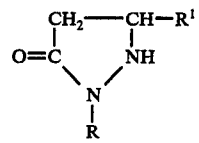

wherein R and $R^1$ have the meanings stated above with hydrogen peroxide in the presence of alkali.

The new process provides a method of manufacture of pyrazolones which avoids the use of β-ketoesters. In many cases it provides a much cheaper route to these valuable compounds than those established in industry.

9 Claims, No Drawings

PROCESS FOR THE MANUFACTURE OF PYRAZOLONES FROM PYRAZOLIDONES

This invention relates to a new process for the manufacture of heterocyclic compounds and is more particularly concerned with the manufacture of pyrazolone compounds by the oxidation of pyrazolidone compounds.

It is known that pyrazolidone compounds when treated with various oxidising agents are converted in part to the corresponding pyrazolones. However the methods described to date also involve the formation of by-products which are difficult to remove and lower the effective yield to an uneconomic level. Thus the use of ferric chloride leads to the simultaneous formation of "pyrazole blue" whilst the use of chloride of lime gives rise to chlorinated by-products.

It has now been found that satisfactory yields of good quality product can be obtained by the use of hydrogen peroxide as oxidising agent.

Thus the present invention provides a process for the manufacture of pyrazolones by oxidation of pyrazolidones, wherein hydrogen peroxide is used as oxidising agent.

The new process can be used for the manufacture of a wide range of pyrazolones and is particularly useful for the conversion of pyrazolidones of the formula

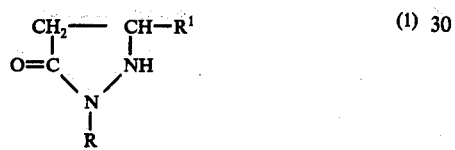

to pyrazolones of the formula:

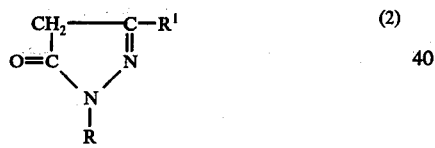

wherein R is an aromatic radical and $R^1$ is an alkyl, carboxylic acid, carbamoyl or carboxylic ester group, which are valuable for use as intermediate compounds in the synthesis of azo dyestuffs.

As examples of aromatic groups represented by R, there may be mentioned carbocyclic groups, more especially groups of the benzene or naphthalene series e.g. phenyl or α or β-naphthyl, which may be substituted, e.g. by $CH_3$, $OCH_3$, Cl, Br, $NO_2$, $CO_2H$ or, above all, $SO_3H$; also heterocyclic radicals e.g. 2-pyridyl and 2-benzthiazolyl. Where R is a substituted phenyl radical it is preferred that the ortho positions are unsubstituted, i.e. that any substituents are placed in the meta and/or para positions.

As examples of groups represented by $R^1$ there may be mentioned, more especially alkyl groups of 1 to 6 carbon atoms, e.g. ethyl, n-propyl, iso-propyl, n-butyl and n-hexyl and, preferably, methyl, and as examples of ester groups, alkyl esters having 1 to 4 carbon atoms in the alkyl group. The preferred meaning of $R^1$ is $CH_3$ or CO.OH.

The new process can conveniently be carried out by dissolving or suspending the pyrazolidone in a hot, aqueous alkaline medium, optionally in the presence of water-miscible organic liquids which are inert to the action of alkali and hydrogen peroxide, and adding the hydrogen peroxide to effect oxidation. The reaction is preferably carried out at a pH of at least 11, e.g. by addition of caustic alkali or the alkali metal salt of a weak acid, e.g. trisodium phosphate or sodium silicate. The preferred alkali is sodium hydroxide. The alkali can be added portionwise during reaction or an excess added at the start of the process.

Whilst we do not wish to be bound by this theory, it is believed that the reaction takes place by a sequence of steps in which the pyrazolidone ring is opened by the addition of the hot, aqueous alkali, and the resultant β-hydrazino carboxylic acid is oxidised to form a hydrazone which then recyclises to form a pyrazolone ring, for example:

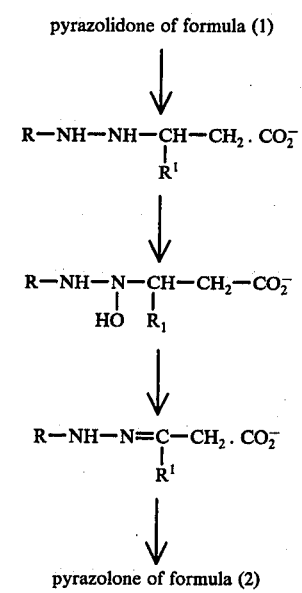

As specific examples of pyrazolidones which may be used, there may be mentioned:
3-methyl-1-phenylpyrazolidone,
3-methyl-1-(4'-sulphophenyl)pyrazolidone,
3-carboxy-1-(4'-sulphophenyl) pyrazolidone,
3-carboxy-1-phenylpyrazolidone,
3-carboxy-1-p-tolylpyrazolidone,
3-methyl-1-p-tolylpyrazolidone,
3-methyl-1-m-sulphophenylpyrazolidone,
3-methyl-1-m-chlorophenylpyrazolidone,
3-n-propyl-1-phenylpyrazolidone,
3-iso-propyl-1-phenylpyrazolidone,
3-n-hexyl-1-phenylpyrazolidone, 3-methyl-1-(2,5-dichloro-4-sulphophenyl)pyrazolidone, and
3-carboxy-1-(3-phosphonophenyl)pyrazolidone.

The pyrazolidones used may be made by methods described in the literature or known from use in practice; in the general case, a pyrazolidone of formula (1) can be made by heating together a phenylhydrazine of the formula $R.NH.NH_2$ and an α;β-unsaturated ester of the formula $R^2CH=CH.CO_2$ alk, where alk is an alkyl group, especially methyl or ethyl, and $R^2$ is either the group $R^1$ or a group which is readily convertible thereto, e.g. where $R^1$ is a COOH group, $R^2$ could be $CO_2H$, $CO_2$ alk or $CO_2NH_2$. In many cases, this reaction also can take place in an aqueous medium, but under slightly acid or neutral conditions, so that the product can be converted in situ and without isolation, to the desired pyrazolone.

Thus the present invention also provides a process for the manufacture of pyrazolones which comprises heating together an aromatic hydrazine and acrylic acid, an acrylic ester or a β-substituted acrylic acid or ester under neutral or acidic aqueous conditions to form a condensation product thereof, basifying the mixture and heating in the presence of alkaline hydrogen peroxide to form the pyrazolone.

As examples of aromatic hydrazines which may be used, there may be mentioned phenylhydrazine, 4-sulphophenyl hydrazine, p-tolylhydrazine, m-sulphophenylhydrazine, m-chlorophenylhydrazine, 2,5-dichloro-4-sulphophenylhydrazine and m-hydrazinobenzene phosphonic acid.

As examples of acrylic esters or β-substituted acrylic esters and acids which may be used there may be mentioned: methyl acrylate, methylmaleic acid or its mono- or di-methyl or mono- or di-ethyl ester, ethylmaleic acid or its mono- or di-methyl ester, crotonic acid and its methyl ester, and methyl- or dimethyl-maleate.

The new process provides a method of manufacture of pyrazolones which avoids the use of β-ketoesters. In many cases it provides a much cheaper route to these valuable compounds than those established in industry.

The invention is illustrated by the following Examples in which parts and percentages are by weight:

EXAMPLE 1 (using isolated pyrazolidone)

12.4 parts of 3-carboxy-(4'-sulphophenyl)-5-pyrazolidone are dissolved in 100 parts of water containing 5 parts of sodium hydroxide and the solution is heated to reflux. The pH of the mixture is adjusted to 11.0–12.0 by the addition of aqueous sodium hydroxide (70° Tw) and is maintained at this pH by the portionwise addition of further aqueous sodium hydroxide. When the pH remains constant at 11.0–12.0 the mixture is cooled to 50° C and hydrogen peroxide 2 parts (at 100%) is added over 3 hours whilst allowing the temperature to rise to 65° C. The temperature is then allowed to rise to 90° C over a further 2 hours and held at this temperature for 1 hour. During this time the pH is kept at 11.0–12.0. After cooling to 70° C and destroying any excess peroxide with sodium bisulphite, sufficient concentrated hydrochloric acid is added to completely precipitate the required product. The product is filtered off at 25° C and dried at 100° C. The actual weight yield is 13.2 parts of strength 86% (determined by titration with sodium nitrite) which represents a yield of 91.5% of theory of 3-carboxy-1-(4'-sulphophenyl)-5-pyrazolone.

EXAMPLE 2 (using isolated pyrazolidone)

25 Parts of 3-methyl-(4'-sulphophenyl)-5-pyrazolidone are added to 200 parts of water containing 10 parts of sodium hydroxide and the mixture is heated to reflux. The pH of the mixture is adjusted to 11.0–12.0 by the addition of aqueous sodium hydroxide (70° Tw) and is maintained at this pH by the portionwise addition of further aqueous sodium hydroxide. When the pH remains constant at 11.0–12.0 the mixture is cooled to 50° C and hydrogen peroxide 3.4 parts (at 100%). The temperature is held at 65° C for 2.5 hours and then raised to 100° C for sodium bisulphite, the mixture is made strongly acidic with excess concentrated hydrochloric acid. Evaporation of the solvent leaves an actual weight yield of 36.2 parts of strength 50.3% (determined by titration in sodium nitrite) which represents a yield of 73.4% of theory of 3-methyl-1-(4'-sulphophenyl)-5-pyrazolone.

EXAMPLE 3 ('in situ' oxidation)

188 Parts of p-hydrazinobenzene sulphonic acid are added with stirring to 470 parts water, heated to reflux and dissolved by the addition of sodium hydroxide. The pH is then adjusted to 5.5 by the addition of a slight excess of sodium hydroxide.

130 Parts monomethylmaleate are added to this solution over 1.½ hr, the pH being maintained at 5.5 by the addition of aqueous sodium hydroxide.

The resulting solution is boiled under reflux for 9 hr, then the pH is adjusted to 11.0–12.0 with aqueous sodium hydroxide and boiled for a further 15 min. keeping the pH at 11–12 by the addition of further aqueous sodium hydroxide.

The solution is then cooled to ca. 60° C and a mixture of 34 parts of hydrogen peroxide in 89.5 parts of water is added over 1.½ hr, after which the temperature is raised over 1 hour to 95° C and held for 1.½ hr. The resultant mixture is then boiled under reflux for 5 min. to complete the reaction and cooled to 50° C.

Sodium bisulphite is added to destroy any excess hydrogen peroxide and sufficient HCl added dropwise to precipitate the required 3-carboxy-1-(4'-sulphophenyl)-5-pyrazolone.

The resulting precipitate is filtered at 25° C and dried at 50°–100° C. The actual weight yield of product is 312 parts of strength 64.3% (as determined by titration with sodium nitrite) which represents a yield of 70.6% of theory from hydrazine.

EXAMPLE 4

20 Parts of 3-methyl-1-phenyl pyrazolidone are added to 70 parts of water and 20 parts of 70° Tw sodium hydroxide solution. The mixture is then boiled for 15 mins. maintaining the pH at 11.0–12.0 with further addition of sodium hydroxide solution as necessary.

The mixture is then cooled to 48° C and 13 parts of hydrogen peroxide are added over 1.½ hours, after which the temperature is raised to 60° C and held for 1 hour.

The temperature is then gradually increased to 80° C over 1 hour and finally to 100° C and held for a further 1 hour, ensuring that the pH is still 11.0–12.0. The solution is then cooled to 5° C and the pH carefully adjusted to 7.0 by concentrated hydrochloric acid. The precipitated 3-methyl-1-phenyl-pyrazol-5-one is filtered at 25° C and dried in a vacuum dessicator.

The actual weight yield is 15.2 parts of strength 95.5% (as determined by titration in sodium nitrite) which represents a yield of 73.3% of theory.

EXAMPLE 5

A mixture of 188 parts of p-hydrazino-benzene sulphonic acid, 86 parts of crotonic acid and 53 parts of anhydrous sodium carbonate in 350 parts of water is refluxed for 48 hours. Whilst still maintaining reflux, the pH is then adjusted to 11.0–12.0 by the addition of aqueous sodium hydroxide (70° Tw) and is maintained at this pH by the portionwise addition of further aqueous sodium hydroxide. When the pH remains constant at 11.0–12.0, the mixture is cooled to 50°–60° C and hydrogen peroxide 34 parts (at 100%) is added over 1.0–1.5 hours. The temperature is then raised to 90° over 2 hours and held at this temperature for 3 hours. During these procedures the pH is kept at 11.0–12.0. After cooling to 70° and destroying any peroxides with sodium bisulphite sufficient concentrated hydrochloric acid is added to precipitate 3-methyl-1-(4'-sulphophenyl)-5-pyrazolone which is filtered at 25° C and dried at 100° C. The actual weight yield is 280 parts of strength 74.8% (determined by titration with sodium nitrite) which represents a yield of 82.4% of theory.

EXAMPLE 6

206 parts of 3-carboxy-1-phenyl-5-pyrazolidone are treated in a similar manner to that described in Example 1. The actual weight yield is 259.7 parts of strength 73.5% (determined by titration with sodium nitrite) which represents a yield of 93.5% of theory of 3-carboxy-1-phenyl-5-pyrazolone.

EXAMPLE 7

220 parts of 3-carboxy-1-(4'-methylphenyl)-5-pyrazolidone are treated in a manner similar to that described in Example 1. The actual weight yield is 264 parts of strength 73% (by titration with sodium nitrite) which represents a yield of 88.4% of theory of 3-carboxy-1-(4'-methylpheny)-5-pyrazolone.

EXAMPLE 8

7 parts of 3-methyl-1-(4'-methylphenyl)-5-pyrazolidone are treated in a similar manner to that described in Example 1. The actual weight yield is 6.3 g of strength 91.3% (determined by titration with sodium nitrite solution which represents a yield of 88% of 3-methyl-1-(4'-methylphenyl)-5-pyrazolone.

EXAMPLE 9

A mixture of 14.5 parts m-hydrazino-benzene sulphonic acid and 6.6 parts of crotonic acid is treated in a manner similar to that described in Example 5. The actual weight yield is 27 parts of strength 59.6% (by titration with sodium nitrite which represents a yield of 83% of theory of 3-ethyl-1-3'-sulphophenyl)pyrazol-5-one.

EXAMPLE 10

6.1 parts of 3-methyl-1-(3'-chlorophenyl)-pyrazolid-5-one are treated in a manner similar to that described in Example 1. The actual weight yield is 8.0 parts of strength 60.3% (by titration with sodium nitrite) which represents a yield of 80.4% of theory of 3-methyl-1-(3'-chlorophenyl)-pyrazol-5-one.

EXAMPLE 11

25 parts of 3-n-propyl-1-phenylpyrazolid-5-one are treated in a manner similar to that described in Example 1. The actual weight yield is 22 parts of strength 97% (by titration with sodium nitrite) which represents a yield of 81.6% of theory of 3-n-propyl-1-phenyl-pyrazol-5-one.

EXAMPLE 12

22.7 parts of 3-isopropyl-1-phenylpyrazolid-5-one are treated in a manner similar to that described in Example 1. The actual weight yield is 15 parts of strength 72.2% (by sodium nitrite) which represents a yield of 48.1% of theory of 3-iso-propyl-1-phenylpyrazol-5-one.

EXAMPLE 13

30 parts of 3-n-hexyl-1-phenylpyrazolid-5-one are treated in a manner similar to that described in Example 1. In this Example, however, the reaction mixture is maintained at reflux during the addition of hydrogen peroxide. The actual weight yield is 31.5 parts of strength 54% (by titration with sodium nitrite) which represents a yield of 57.1% of theory of 3-n-hexyl-1-phenylpyrazol-5-one.

What we claim is:

1. A process for manufacture of pyrazolones of the formula:

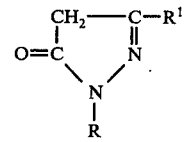

wherein R is an aromatic radical selected from the group consisting of phenyl, α- and β- naphthyl, and phenyl, α- and β-naphthyl substituted with $CH_3$, $OCH_3$, Cl, Br, $NO_2$, $CO_2H$ or $SO_3H$ and $R^1$ is alkyl of 1–6 carbon atoms, carboxylic acid, or carboxylic acid alkyl ester having 1 to 4 carbon atoms in the alkyl group which comprises treating a pyrazolidone of the formula:

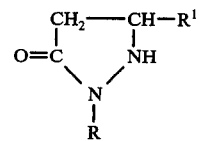

wherein R and $R^1$ have the meanings stated above with hydrogen peroxide in the presence of alkali.

2. A process as claimed in claim 1 wherein R is phenyl.

3. A process as claimed in claim 1 wherein R is a substituted phenyl carrying the substituent or substituents in the meta- and/or para-positions of the benzene nucleus.

4. A process as claimed in claim 1 wherein $R^1$ is $CH_3$ or COOH.

5. A process as claimed in claim 1 which is carried out at a pH of 11 or higher.

6. A process as claimed in claim 1 wherein the pyrazolidone is selected from
   3-methyl-1-phenylpyrazolidone,
   3-methyl-1-(4'-sulphophenyl)pyrazolidone,
   3-carboxy-1-(4'-sulphophenyl)pyrazolidone,
   3-carboxy-1-phenylpyrazolidone,
   3-carboxy-1-p-tolylpyrazolidone,
   3-methyl-1-p-tolylpyrazolidone,
   3-methyl-1-m-sulphophenylpyrazolidone,
   3-methyl-1-m-chlorophenylpyrazolidone,
   3-n-propyl-1-phenylpyrazolidone,
   3-iso-propyl-1-phenylpyrazolidone,
   3-n-hexyl-1-phenylpyrazolidone,
   3-ethyl-1-(2,5-dichloro-4-sulphophenyl)pyrazolidone, and
   3-carboxy-1-(3-phosphonophenyl)pyrazolidone.

7. A process as claimed in claim 1 which comprising heating together an aromatic hydrazine and acrylic acid, an acrylic ester or a β-substituted acrylic acid or ester under neutral or acidic aqueous conditions to form a condensation product thereof, basifying the mixture and heating in the presence of alkaline hydrogen peroxide to form the pyrazolone.

8. A process as claimed in claim 7 wherein the aromatic hydrazine is selected from phenylhydrazine, 4-sulphophenylhydrazine, p-tolylhydrazine, m-sulphophenylhydrazine, m-chlorophenylhydrazine, 2,5-dichloro-4-sulphophenylhydrazine and m-hydrazinobenzene phosphonic acid.

9. A process as claimed in claim 7 wherein there is used methyl acrylate, methylmaleic acid or its mono- or di-methyl or mono- or di-ethyl ester, ethylmaleic acid or its mono- or di-methyl ester, crotonic acid or its methyl ester, or methyl- or dimethyl-maleate.

* * * * *